(12) United States Patent
Collins et al.

(10) Patent No.: US 8,535,738 B2
(45) Date of Patent: Sep. 17, 2013

(54) METHODS AND COMPOSITIONS FOR TREATING SKIN

(75) Inventors: Donald F. Collins, Plainview, NY (US); Daniel H. Maes, Huntington, NY (US); Neelam Muizzuddin, Bethpage, NY (US)

(73) Assignee: ELC Management, LLC, New York, NY (US)

( * ) Notice: Subject to any disclaimer, the term of this patent is extended or adjusted under 35 U.S.C. 154(b) by 378 days.

(21) Appl. No.: 12/743,500

(22) PCT Filed: Jul. 7, 2008

(86) PCT No.: PCT/US2008/069323
§ 371 (c)(1),
(2), (4) Date: Aug. 4, 2010

(87) PCT Pub. No.: WO2009/082511
PCT Pub. Date: Jul. 2, 2009

(65) Prior Publication Data
US 2010/0323042 A1    Dec. 23, 2010

Related U.S. Application Data

(60) Provisional application No. 61/015,250, filed on Dec. 20, 2007.

(51) Int. Cl.
*A61K 8/63* (2006.01)
(52) U.S. Cl.
USPC .......................................... 424/750; 424/735
(58) Field of Classification Search
None
See application file for complete search history.

(56) References Cited

U.S. PATENT DOCUMENTS

| | | | |
|---|---|---|---|
| 3,439,088 A | 4/1969 | Edman | |
| 3,818,105 A | 6/1974 | Coopersmith et al. | |
| 4,677,152 A | 6/1987 | Allen et al. | |
| 4,702,844 A | 10/1987 | Flesher et al. | |
| 4,970,252 A | 11/1990 | Sakuta et al. | |
| 5,236,986 A | 8/1993 | Sakuta | |
| 5,412,004 A | 5/1995 | Tachibana et al. | |
| 5,654,362 A | 8/1997 | Schulz, Jr. et al. | |
| 5,760,116 A | 6/1998 | Kilgour et al. | |
| 5,811,487 A | 9/1998 | Schulz, Jr. et al. | |
| 5,837,793 A | 11/1998 | Harashima et al. | |
| 5,843,193 A | 12/1998 | Hawkins et al. | |
| 6,881,756 B2 | 4/2005 | Gendimenico | |
| 2003/0105063 A1* | 6/2003 | Perricone | 514/78 |
| 2004/0121031 A1 | 6/2004 | Majeed et al. | |
| 2005/0100537 A1* | 5/2005 | Evans et al. | 424/94.1 |
| 2005/0101632 A1* | 5/2005 | Gagnon et al. | 514/313 |
| 2006/0034875 A1 | 2/2006 | Nakanishi et al. | |
| 2006/0257337 A1* | 11/2006 | Sherris | 424/59 |
| 2008/0286298 A1 | 11/2008 | Chen et al. | |
| 2010/0015072 A1 | 1/2010 | Polla et al. | |
| 2010/0047295 A1 | 2/2010 | Giagnorio | |

FOREIGN PATENT DOCUMENTS

| | | |
|---|---|---|
| CN | 101473952 | 7/2009 |
| CN | 101589802 | 12/2009 |
| EP | 1908358 | 4/2008 |
| JP | 61-018708 | 1/1986 |
| JP | 2003267887 | 9/2003 |
| KR | 20070001359 | 1/2001 |
| WO | WO2004/024798 | 3/2004 |

OTHER PUBLICATIONS

PCT International Search Report; International Application No. PCT/US2008/069323; Completion Date: Jan. 29, 2009; Date of Mailing. Jan. 29, 2009.
PCT Written Opinion of the International Searching Authority, or the Declaration; International Application No. PCT/US2008/069323; Completion Date: Jan. 29, 2009; Date of Mailing: Jan. 29, 2009.
Nathan, Carl; Nature; vol. 420; Insight Review Articles; Points of control in inflammation; Dept. of Microbiology and Immunology; pp. 846-852; www.nature.com/nature; Dec. 2002.
PCT International Search Report; International Application No. PCT/US2010/026561; Completion Date: Dec. 23, 2010; Date of Mailing: Dec. 23, 2010.
PCT Written Opinion of the International Searching Authority; International Application No. PCT/US2010/026561; Completion Date: Dec. 23, 2010; Mailing Date: Dec. 23, 2010.

* cited by examiner

*Primary Examiner* — Lisa J Hobbs
(74) *Attorney, Agent, or Firm* — Julie M. Blackburn

(57) ABSTRACT

A method for formulating products to normalize skin or treat irritated or inflamed skin, a method for normalizing skin or treating irritated or inflamed skin for improvement, and compositions therefor.

20 Claims, 1 Drawing Sheet

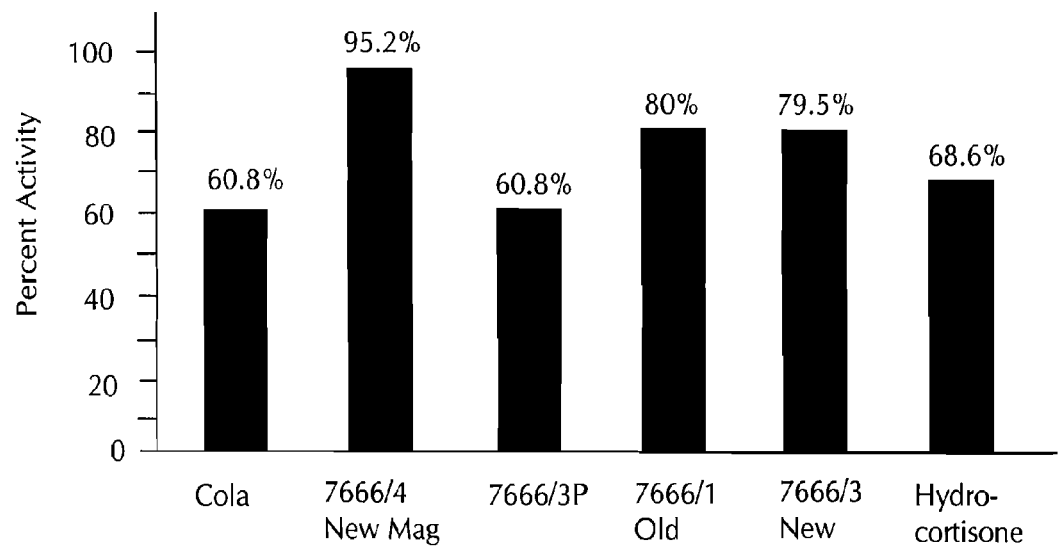

METHODS AND COMPOSITIONS FOR TREATING SKIN

This application is a national stage filing of PCT/US2008/069323, filed Jul. 7, 2008, and claims priority from US61/015,250, filed Dec. 20, 2007.

TECHNICAL FIELD

The invention is in the field of formulating compositions for treating skin and the resulting skin care compositions.

BACKGROUND OF THE INVENTION

Skin is the largest and one of the most complex body organs. It comprises from about 15 to 20% of the entire body weight and serves as a protective barrier to environmental toxins and assaults. Very few people are satisfied with their skin condition, particularly facial skin. Skin care product companies have made a big business out of treating common skin maladies such as dryness, oiliness, uneven pigmentation, wrinkles, laxity and the like. Skin that is in good health is referred to as normalized skin. The skin's immune response to environmental conditions such as excessive sun exposure, cold weather, wind, or cigarette smoke can have an effect on skin. In some cases skin may become irritated or inflamed—in other words the skin is no longer normalized. For years cosmetics manufacturers have sold products for normalizing skin that included ingredients believed to have anti-inflammatory or anti-irritant properties. However, since there are a myriad of biological reactive pathways that contribute to skin inflammation and these products often contained ingredients that did not have any impact on any of these reactive pathways, they were not often as effective as they could have been. For example, one immune response of assaulted tissue is histamine release, predominantly by basophilic cells. Another reactive pathway that contributes to skin inflammation is release of cyclooxygenase-2 (also referred to as COX-2), an enzyme known to promote inflammation and pain. Yet another reactive pathway that contributes to skin inflammation is the release of an enzyme, phospholipase-2 (PLA-2) by cells and tissue subjected to immune assaults. Current skin care products may or may not contain ingredients that have inhibitory effects on these reactive pathways. Accordingly, such products may not be optimally effective in normalizing skin.

There is a need for compositions for normalizing skin, that is, treating skin that may be inflamed, irritated, or in otherwise a less than optimal state of health, to obtain improvement.

It is an object of the invention to provide a method for formulating products to normalize skin, or treating irritated or inflamed skin for improvement. Such method includes identifying one or more reactive pathways that contribute to skin inflammation and selecting one or more ingredients that inhibit the pathways selected and formulating the selected ingredients into a composition that when topically applied exhibits skin normalizing properties.

It is a further object to provide a method for normalizing skin, or treating irritated or inflamed skin for improvement comprising applying to the skin a composition that has been formulated by identifying a plurality of pathways that contribute to inflammation and selecting at least one ingredient that inhibits each of the pathways identified and formulating the plurality of selected ingredients into a composition.

It is a further object of the invention to provide a composition for normalizing skin or treating skin irritation or inflammation comprising a plurality of ingredients that are selected to inhibit a plurality of pathways that contribute to skin inflammation.

SUMMARY OF THE INVENTION

The invention is directed to a method for formulating compositions for normalizing skin comprising identifying a plurality of pathways that contribute to skin inflammation, selecting ingredients that inhibit the pathways identified and formulating the selected ingredients into a composition that when topically applied exhibits skin normalizing properties.

The invention is also directed to a method for formulating compositions for treating skin irritation or inflammation comprising identifying a plurality of pathways that contribute to skin inflammation, selecting one or more ingredients that inhibit the pathways identified and formulating the selected ingredients into a composition that when topically applied ameliorates the undesired effects of skin irritation or inflammation.

The invention is further directed to a method for normalizing skin comprising applying to the skin a composition that has been formulated by identifying a plurality of pathways that contribute to inflammation, selecting ingredients that inhibit the pathways identified and formulating the selected ingredients into a composition that provides skin normalizing properties.

The invention is further directed to a method for treating irritated or inflamed skin comprising applying to the skin a composition that has been formulated by identifying a plurality of pathways that contribute to skin inflammation, selecting ingredients that inhibit the pathways identified and formulating the ingredients into a composition that ameliorates the adverse effects of skin irritation or inflammation.

The invention is also directed to a composition for normalizing skin comprising a plurality of ingredients that are selected to inhibit a plurality of pathways that contribute to skin inflammation.

The invention is also directed to a composition for treating skin irritation or inflammation comprising a plurality of ingredients that are selected to inhibit a plurality of pathways that contribute to skin inflammation.

DESCRIPTION OF THE FIGURE

The FIGURE compares the effectiveness of several compositions at inhibiting inflammation.

DETAILED DESCRIPTION

I. Definitions

"Adhesion Pathway" is the pathway by which cells adhere to blood vessels and other skin tissues when injury or immune challenge has occurred.

"Chemotaxis Pathway" means the pathway where chemical signals cause inflammatory cells to migrate toward the site in the body, such as skin or tissue, where immune challenge has occurred. If such inflammatory cells are prevented from migrating to the site of immune challenge the resulting damage that such cells provide to skin or tissues can be mitigated.

"Collagenase Pathway" means the pathway by which the enzyme collagenase breaks down the peptide bonds in collagen and destroys extracellular structures such as those found in bacteria or infiltrating lymphocytes at the sites of inflammation. The collagenases released will cause tissue damage by breaking down collagen fibrils in the extra cellular matrix.

"COX Pathway" means the pathway by which the cyclooxygenase (COX) enzyme (including but not limited to cyclooxygenase-2 or COX-2) converts arachidonic acid and/or other fatty acids to prostaglandin or prostanoids which ultimately contributes to inflammation or pain in immune challenged tissue such as skin.

"Elastase Pathway" means the pathway by which the enzyme elastase degrades proteins including elastin that are found in bacteria and other molecules. When the Elastase Pathway is triggered the cascade of reactions contributes to inflammation or pain in immune challenged tissue such as skin. Elastase, a peptidase released from infiltrating neutrophils at the site of inflammation, will break down elastin, an elastic fiber that, together with collagen, helps determine the mechanical properties of skin and other tissues. Inhibition of elastase will minimize the damage that may be caused by infiltrating neutrophils which in turn will help preserve the integrity of the extra cellular matrix.

"Histamine Pathway" means the pathway where the amino acid histidine is decarboxylated to form histamine in response to immune challenge or other injury to tissue or skin. Histamine is a biogenic amine that is synthesized and stored in mast cells which reside primarily in the skin. Histamine plays a major role in the initiation of the inflammatory cascade. Upon stimulation, mast cells (and basophils) will release their stored histamine which will bind to H1 receptors on a variety of cells (including smooth muscle cells and endothelial cells in blood vessels) exerting its biologic effects. These effects include vasodilation, separation of endothelial cells (causing abnormal vascular permeability), pain and itching. Inhibition of histamine release provides amelioration from many of the adverse effects of inflammation.

"Histamine Receptor Pathway" means that pathway by which cellular receptors for histamine are activated to bind to histamine, which in turn contributes to the inflammatory condition of tissues or skin.

"Immune challenged" means tissues or skin subjected to environmental, bacterial or viral assaults and where any one or more of the Pathways that contribute to inflammation have been triggered.

"Inflammation" means, when used to describe skin, that the skin has been subjected to moderate to severe environmental or chemical assault and is moderately to severely immune challenged. Examples of inflammation include sunburn, windburn, acne, insect bites, cuts, burns, rosacea, and the like. Inflammation typically produces one or more of redness, pain, and heat in the skin.

"Inhibitor" means, when used with a particular Pathway, an ingredient or combination of ingredients that inhibits the Pathway in whole or in part. For example, Histamine Pathway Inhibitor means an ingredient or combination of ingredients that inhibits the Histamine Pathway in whole or in part.

"Irritation", when used to describe skin, means that the skin has been aggravated by environmental assaults or toxins, or application of products containing one or more ingredients to which the skin is sensitized or otherwise incompatible. Irritation may result in redness, itchiness, dryness, blemishes, enlarged pores, and so on. Irritated skin may also exhibit one or more of redness, pain, and heat.

"LO Pathway" means the pathway by which the enzyme lipooxygenase, preferably 5-lipooxygenase, catalyzes the conversion of arachidonic acid to 5-hydroperoxyeicosatetraenoic acid and then to leukotriene A4, which ultimately contributes to inflammation or pain in immune challenged tissue such as skin.

"Liquid" means a composition that is a pourable liquid at room temperature.

"Non-volatile" means that the ingredient has a vapor pressure of less than about 2 mm. of mercury at 20° C.

"Normal" or "Normalized", when used to describe skin, means skin that is in its optimum state of natural health. Normalizing skin can include treating skin to improve irritation or inflammation, or ameliorate or relieve conditions such as dark under eye circles, or to improve the appearance of wrinkles, lines, uneven pigmentation, sallowness, dryness, laxity, mottled skin, age spots, and the like.

"Pathway", when used with respect to inflammation, means a cascade of reactions that occurs when skin or tissue is exposed to immune challenge, and which ultimately contributes to skin inflammation.

"PDE Pathway" means that pathway by which PDE (phosphodiesterase) including phosphodiesterase-4 (PDE4) cleaves the phosphodiester bond that may be found in proteins and other molecules present in bacteria, viruses, and other molecules that contribute to skin inflammation. PDE4, in particular, is a member of a family of enzymes that catalyze the degradation of cAMP to the corresponding 5'-nucleotide monophosphate. PDE4 is abundant and is the major regulator of cAMP metabolism in almost every pro-inflammatory and immune cell. PDE4 inhibitors exert their anti-inflammatory effects by inhibiting the breakdown of cAMP (leading to an increased concentration of cAMP in immune cells) which will ultimately lead to a decrease in the production and release of pro-inflammatory cytokines such as Interleukin 1-β (IL-1β) and Tumor Necrosis Factor α (TNFα).

Percentages mentioned herein shall mean percentage by weight unless otherwise indicated.

"PLA-2 Pathway" means the pathway by which the phospholipase A2 (PLA-2) enzyme hydrolyzes phospholipids to form fatty acid lysophospholipid products such as arachidonic acid, which ultimately converts to leukotrienes and prostaglandins, which contribute to the inflammatory response in immune challenged tissue such as skin.

"Plurality" means more than one.

"Semi-solid" means a composition that exists in a cream or paste and which is neither pourable or solid at room temperature.

"Solid" means a composition that is a solid at room temperature (e.g. 25° C.).

"VEGF Pathway" means the pathway by which VEGF (vascular endothelial growth factor) causes angiogensis (the formation of blood vessels) in immune challenged skin. In addition to inducing angiogenesis, VEGF also is responsible for increasing vascular leakage which will lead to increased edema in damaged tissue or skin.

"Volatile" means that the ingredient has a vapor pressure of about 2 mm. of mercury or greater at 20° C.

II. The Methods

The methods of invention include a method for formulating compositions to treat inflamed or irritated skin, or to treat skin to achieve normalization. In the method of the invention, a plurality of the Pathways that contribute to skin inflammation are identified and ingredients that inhibit the identified Pathway, either in whole or in part are selected and formulated into compositions that are then applied to the skin to treat the skin irritation or inflammation, or to otherwise normalize the skin. Some ingredients have functionality in inhibiting more than one Pathway. In that case that one ingredient may be incorporated into the composition in an amount sufficient to exert an inhibitory effect on the plurality of Pathways identified.

At this time, the Pathways that contribute to inflammation are believed to be the Adhesion Pathway, the Chemotaxis Pathway, the Collagenase Pathway, the COX Pathway, the Elastase Pathway, the Histamine Pathway, the Histamine Receptor Pathway, the LO Pathway, the PDE Pathway, the PLA-2 Pathway, and the VEGF Pathway. However, this invention is construed to include pathways that are not identified herein, or may in the future be identified, or pathways that may be described herein in different terms, or as part of larger pathways not fully mentioned herein.

A. Adhesion Pathway

One Pathway that is believed to contribute to inflammation is the Adhesion Pathway. When skin is injured, cells migrate to the area of injury as part of the immune response. Such cells adhere to the site of the injury to close off broken blood vessels, protect tissues, or otherwise aid in the healing response. Accordingly, ingredients that inhibit the Adhesion Pathway in whole or in part are selected for formulation in the composition. Such ingredients may be in the form of botanical extracts, chemical compounds, polymers, and the like. Adhesion Pathway Inhibitors may be present in the formulated compositions in amounts ranging from about 0.0001 to 75%, preferably from about 0.001 to 70%, more preferably from about 0.005 to 20%.

One test that is suitable for determining whether a selected ingredient may inhibit the Adhesion Pathway is based upon the analysis of the adhesion of polymorphonuclear cells (PMN) to human dermal microvasicular cells—one of the things that occurs when leukocytes migrate to a site of irritation or infection in tissue that has been subject to assault. The test is conducted by collecting heparinized peripheral venous blood (about 20-30 ml) from healthy human donors who are requested to refrain from caffeine intake for 12 hours prior to the blood drawing. The heparinized blood from each individual is layered over a density gradient (Mono-Poly Resolving Media, sold by ICN Pharmaceuticals, Costa Mesa, Calif.) and spun at 400×g for 30 minutes. The PMN cell rich fraction is removed and the red blood cells lysed with hypotonic saline. The PMN fraction is washed twice with Hank's balanced salt solution (HBSS) and then re-suspended in 5.0 ml HBSS (with ions), which has been supplemented with 0.4% bovine serum albumin (Sigma Aldrich). The concentration of cells is adjusted to $10 \times 10^6$ PMN/ml. Collected PMN are greater than 95% pure and 98% viable as assessed by the Trypan Blue Exclusion Test of Cell Viability, a test well known in the art. Human dermal microvasicular endothelial cells (HDMEC) are obtained from the Clonetics Corporation and maintained according to specifications until confluent. The PMNs at a concentration of $4 \times 10^6$/ml are mixed 1:1 with the test material (final concentration of cells=$2 \times 10^6$/ml) and incubated for 30 minutes with the test material. The appropriate concentration of material to be tested is determined by conducting standard cytotoxicity tests to identify the highest concentration of test material that causes cytotoxicity. After this upper limit has been established successive serial dilutions of the test material are tested.

After a 30 minute incubation with the test material plus tetradecanoyl phorbol acetate (TPA, 5 ng/ml) or, for control, with test material alone, or with TPA alone or vehicle; the PMN (350,000/well) are added to wells of a 96-well microtiter plate in which endothelial cells are seeded at 20,000 cells/well and allowed to reach confluence. The endothelial cells are activated by pre-incubating with Interleukin-1β (10 U/ml) for 60 minutes at 37° C. in 5% $CO_2$. After the two cell types have been in contact for two hours the supernatant is removed, remaining cells gently rinsed, and 100 ml of 0.25% rose bengal (ICN) stain in PBS is added for 5 minutes at room temperature. Non-adherent cells are removed by two subsequent washes (Medium 199 with 25 mM HEPES and 10% fetal bovine serum). Stain incorporated into cells is released by the addition of 200 ml of a 1:1 solution of ethanol and PBS. After 30-45 minutes the wells are read in an ELISA reader (Bio-Tek Instruments Inc. Winooski, Vt.) at 570 nm. The level of adherence is given as the mean optical density reading at an OD570 for wells containing endothelial cells plus PMN minus the mean OD570 of wells containing endothelial cells alone.

While the above test is suitable for ascertaining which selected ingredients inhibit the Adhesion Pathway, other tests, either now known or hereafter developed may be suitable so long as they accurately identify ingredients that are capable of inhibiting the Adhesion Pathway.

Various ingredients have inhibitory activity for the Adhesion Pathway, including but not limited to Algae extract, neem oil limonoids, *Asparagus Racemusus* extract, *Platycodon* extract, Chaga Mushroom extract, *Emblica Officinalis* extract, *Criste Marine* extract, *Lavande Papillon* extract, *Polygonum Cuspidatum*, ginger, Polysea PF (algae extract purchased from Frutarom), and mixtures of these ingredients.

B. Chemotaxis Pathway

Another Pathway believed to contribute to inflammation is the Chemotaxis Pathway. When skin is injured, cells migrate to the area of injury as part of the immune response. The migration of such cells is called chemotaxis. Ingredients that inhibit the Chemotaxis Pathway in whole or in part, are selected for formulation in the composition. The ingredients may be in the form of botanical extracts, chemical compounds, polymers, and so on. The Chemotaxis Pathway Inhibitors may be present in the composition ranging from about 0.0001 to 75%, preferably from about 0.0005 to 70%, more preferably from about 0.001 to 20%.

One test that may be used to determine whether a particular ingredient inhibits the Chemotaxis Pathway is one that is based upon the ability of a test material to inhibit the migration of PMNs toward a known chemotactic agent.

This test is performed by collecting heparinized peripheral venous blood (20-30 ml) from healthy human donors who are requested to refrain from caffeine intake for 12 hours prior to the blood drawing. The blood sample is layered over a density gradient (mono-poly resolving media, ICN Pharmaceuticals, Costa Mesa, Calif.) and spun at 400×g for 30 min. The PMN rich fraction is removed and the red blood cells lysed with hypotonic saline. The PMN are washed twice with Hank's balanced salt solution (HBSS) and then resuspended in 5.0 ml HBSS with ions supplemented with 0.4% bovine serum albumin (Sigma). The concentration of cells is adjusted to $10 \times 10^6$ PMN/ml. Collected PMNs are greater than 95% pure and 98% viable as assessed by the Trypan Blue Exclusion Assay, which is performed using a Boyden chamber apparatus with blind well chambers fitted with 5 mm pore size filters (Millipore). The apparatus consists of two vertical chambers separated by a filter that contains pores of a size chosen such that the holes are large enough for the cells to actively crawl through them but not so large that the cells can physically fall through into the lower chamber. PMN are then pre-incubated with test compounds at the indicated concentrations. A 200 ml PMN cell suspension is layered on the top of the filter, and 100 ml of chemotactic factors are added to the lower compartment. The chemo-attractant used in the assay is 0.125 nM LTB4. Following incubation at 37° C. for 90 minutes under a humidified atmosphere with 5% $CO_2$, the filters are fixed with propanol and stained with haematoxylin and eosin. The PMN chemotactic response is determined by the distance to the leading front and the number of cells that migrated to the front. The distance to the leading front is determined at 400× magnification by the distance the majority of the cells migrated through the filter. The results are expressed as the average number of cells per high powered field at the leading migratory front (PMN/HPF).

While the above test is suitable for ascertaining which selected ingredients inhibit the Chemotaxis Pathway, other tests, either now known or hereafter developed may be suitable so long as they accurately identify ingredients that are capable of inhibiting the Chemotaxis Pathway.

Examples of ingredients that inhibit the Chemotaxis Pathway include sulfated polysaccharides such as fucoidan, that may be isolated from seaweeds such as kombu, limu, moui, bladderwrack, wakame, mozuku, hijiki, and the like; or animal sources such as sea cucumber. Further examples of Chemotaxis Pathway inhibitors include kelp, sea buckthorn, *Laminaria Japonica, Fucus Vesiculosis*, and the like. Also various vegetable extracts are excellent inhibitors of the Chemotaxis Pathway, including extracts of onions, potatoes, celery, carrots, turnips, parsley, parsnip, sweet potato, yucca, beets, and the like. Other types of Chemotaxis Pathway inhibitors include licorice extracts, genestein, extracts from the genus *Scutellaria* (such a *Scutellaria Baicalensis*), extracts from the *Boswellia* genus such as *Boswellia Serrata, Boswellia Bhau-dajiana, Boswellia Frereana, Boswellia Papyrifera, Sudanese Boswellia Sacra*, and *Boswellia Carteri, Commiphora Incisa, Commiphora Myrrha, Commiphora Abyssinica, Commiphora Erthraea, Commiphora Molmol*, and *Bursera Microphylla; Nidularium Procerum*, sequoia extract, hypoestoxide, *Curcuma Longa* (turmeric) extract, butyloctyl salicylate, abyssine, plai oil, geranium bourbon oil, jiagolun EX, fucoidan YSK, caffeine, galactoarabinan (sold under the tradename Laracare A200), lion's mane mushroom extract, clerilys, and extracts from *Macrycystis Pyrifera*, reishi mushroom, *Pleurotus Ostreatus* extract, *Hypsizygus Ulmarius, Cladosiphon Okamuranus* Extract, *Acalypha Wilkesiana, Acanthopanax Gracilistylus, Allium Sativunt, Ananus Comosus, Cissampelos Sympodialis, Coriolus Versicolor, Echinacea Purpurea, Grifola Frondosa, Harpagophytum Procumbens, Panax Ginseng, Polygala Tenuifolia, Poria Cocos, Silybum Marianum, Smilax Glabra, Tinospora Cordifolia, Uncarta Tomentosa*, and *Withania Somnifera*, slime mold, *Echinancea, Viscum Album*, coffee robusta seed extract, capsaicin, and mixtures thereof.

Suitable inhibitors of the Chemotaxis Pathway may include compounds or molecules such as TAK-661 ((2,2-dimethyl-3-[[7-(1-methylethyl)[1,2,4]triazolo[1,5-b]pyridazin-6-yl]oxy]-1-propanesulfonamide), CCRI antagonist, PD172084, CXCR3 Antagonist. hexapeptide Val-Gly-Val-Ala-Pro-Gly (VGVAPG), a recurring sequence in the elastin molecule ubiquitin, nicotinanalides, Cytochalasin B, C. Collagenase Pathway Another Pathway that is believed to contribute to skin inflammation is the Collagenase Pathway, where the enzyme collagenase is triggered to break down the peptide bonds in collagen to destroy the extracellular structures such as those found in bacteria and viruses that, when in contact with skin or tissues cause injury or immune challenge. Collagenase Pathway Inhibitors will inhibit the activity of the collagenase enzyme so that it will not destroy collagen, for example, the collagen like that found in the cellular or extracellular structures of bacteria or lymphocytes at the site of injury. The Collagenase Pathway Inhibitors may be present in amounts ranging from about 0.0001 to 75%, preferably from about 0.0005 to 70%, more preferably from about 0.001 to 20%.

A simple test that can determine whether a particular ingredient inhibits the Collagenase Pathway is a fluorescent microtiter assay based upon the principle that matrix metalloproteinase-1 (MMP-1), interstitial collagenase, or fibroblast collagenase can cleave the quenched fluorescent peptide OmniMMP™ (Mca-PLGLDpaAR from Biomol) at the Gly-Leu bond. Upon enzymatic cleavage the fluorescent tag is released and the fluorescence increases as the enzymatic reaction progresses. The presence of an MMP-1 inhibitor will cause a reduction in fluorescence. The MMP-1 is obtained from R & D Systems as a proenzyme that must be activated with p-aminophenylmercuric acetate (APMA).

To perform this assay, the following solutions are prepared: Assay Buffer (50 mM Tris, 10 mM $CaCl_2$, 150 mM NaCl, 0.05% Brij, pH 7.5), 400 µM OmniMMP peptide in DMSO, 0.7 µM N-isobutyl-N-(4-methoxyphenylsulfonyl)glycyl hydroxamic acid (NNGH, reference inhibitor from Biomol) in DMSO and 20 mM APMA in DMSO. 100 µg/ml of MMP-1 is activated with APMA at a final concentration of 1 mM (for 1 hour at 37° C. in the dark). After activation, the MMP-1 is diluted to 0.88 µg/ml. The activated MMP-1 is tested at a final concentration of 0.18 µg/ml in the wells of a 96 well plate. Potential inhibitors are tested at final concentration of 200, 100, 50 and 25 µg/ml. The reaction is carried out in a 96 well plate by adding appropriate volumes of activated MMP-1, reference inhibitor or potential inhibitors and incubating in the dark for 1 hour at room temperature. After the 1 hour incubation, the OmniMMp peptide is added to each well to a final concentration of 4 µM. The fluorescence ($320_{ex}/400_{em}$) is then monitored in a fluorescent plate reader for 1 hour. The fluorescence readings for each sample are plotted versus time and the initial reaction velocity is calculated from the initial slope of the fluorescence versus time for each inhibitor concentration. The initial reaction velocity is plotted as a function of the end concentration of the potential inhibitor and the $IC_{50}$ is then calculated. The $IC_{50}$ corresponds to the concentration of inhibitor that results in a 50% reduction of the initial reaction velocity in the absence of the inhibitor.

While the above test is suitable for ascertaining which selected ingredients inhibit the Collagenase Pathway, other tests, either now known or hereafter developed may be suitable so long as they accurately identify ingredients that are capable of inhibiting the Collagenase Pathway.

A variety of ingredients are known to be Collagenase Pathway Inhibitors, including but not limited to those from the *Siegesbeckia* genus such as *Siegesbeckia Orientalis*; the *Doliocarpus* genus such as *Doliocarpus Verruculosus*; the *Kaempferia* genus such as *Kaempferia Galanga* root extract; the *Camilla* genus such as *Camilla Sinensis*; the *Sauropus* genus such as *Sauropus Androgynus*; the *Tetracapidium* genus such as *Tetracapidium Conophorum*; glucosamine, N-acetyl glucoseamine, chondroitan sulfate, *Pinus Pinaster* (pine bark) extract, lysine, *Vitis Vinefera* (grape) seed extract, retinoids such as retinyl palmitate, retinol, retinoic acid; extracts from the *Pluchea* genus such as *Pluchea Indica* (Compositae); the *Viola* genus such as *Viola Hondoensis*; cocoa bean; the *Triphala* genus such as *Triphala Chebula*, anthocyanins, epigallocatechingallate, epicatechingallate, luteolin, *Citri Reticulatae* peel extract, winter begonia extract; the *Tepescohuite* genus, such as *Tepescohuite* spray dried extract; from the *Mimosa* genus such as *Mimosa Pudica* extract, picolinic acid, climmp-19, *Silymarin* extract, *Eucommia* extract, amentoflavone; from the *Menyanthes* genus such as *Menyanthes Trifoliate* extract; or mixtures thereof.

D. COX Pathway

In the COX Pathway the cyclooxygenase (COX) enzyme (including but not limited to cyclooxygenase-2 or COX-2) converts arachidonic acid and/or other fatty acids to prostaglandin or prostanoids. It is these prostaglandins or prostanoids that ultimately contribute to inflammation by causing pain near the sites of the immune challenge or damage. COX Pathway Inhibitors will block the conversion of arachidonic or other fatty acids to prostaglandin or prostanoids in whole or in part. The COX Pathway Inhibitors may be present in amounts ranging from about 0.0001 to 75%, preferably from about 0.0005 to 70%, more preferably from about 0.001 to 20%.

COX-2 is responsible for the biosynthesis of prostaglandins under acute inflammatory conditions. COX-2 is believed to be the target enzyme for the anti-inflammatory activity of nonsteroidal anti-inflammatory drugs. The COX Inhibitor Screening Assay Kit from Cayman Chemical (560131) directly measures $PGF_{2\alpha}$ produced by $SnCl_2$ reduction of COX-derived $PGH_2$. The prostanoid product is quantified via enzyme immunoassay (EIA) using a broadly specific antibody that binds to all the major prostaglandin compounds. The COX Inhibitor Screening Assay was performed as outlined in the protocol supplied by the manufacturer and the results calculated from the standard curve.

While the above test is suitable for ascertaining which selected ingredients inhibit the COX Pathway, other tests, either now known or hereafter developed may be suitable so long as they accurately identify ingredients that are capable of inhibiting the COX Pathway.

A variety of ingredients are COX Pathway inhibitors, including but not limited to extracts of plants from the *Acacia* genus, *Calluna Vulgaris, Rosa Canina* fruit extract, nettle leaf extract, *Polyporus Umbellatus, Chamomilla Recutita* (Matricaria) flower oil, Rusperin C®, (a mixture of Butcher's Broom extract and heperidin methyl chalcone), resveratrol, HOP's beta acids, and mixtures thereof.

E. Elastase Pathway

In the Elastase Pathway, in response to immune challenge or tissue damage the enzyme elastase is released to degrade proteins including elastin that are found in bacteria or invading cells. When the Elastase Pathway is triggered the cascade of reactions also contributes to inflammation or pain in immune challenged tissue such as skin. The Elastase Pathway Inhibitors may be present in amounts ranging from 0.0001 to 75%, preferably from about 0.0005 to 70%, more preferably from about 0.001 to 20%.

A simple test that can be performed to determine whether an ingredient inhibits the Elastase Pathway is performed by using a synthetic elastase substrate (Meo-suc-ala-ala-pro-val-pNa peptide from Sigma) and diluting to 200 µM in Dulbecco's PBS (no Calcium or Magnesium) containing 5% dimethylsulfoxide (DMSO) and 50 µl are added to a 96 well plate. Potential inhibitors are diluted in Dulbecco's PBS (D-PBS) containing 10% DMSO and 5 µl are added to the plate and allowed to equilibrate for 5 minutes at room temperature. Potential inhibitors are typically tested at final concentrations of 1, 10, 100 and 1000 µg/ml for powdered samples and at 0.001, 0.01, 0.1 and 1% (v/v) for liquid samples. Human leukocyte elastase (Sigma) is diluted to 0.005 mg/ml with D-PBS/5% DMSO and 50 µl are added to the wells of the plate. Kinetic readings of the optical density at 405 nm are monitored for 10 minutes and the Vmax is determined. The EC50 for each inhibitor is then calculated. While this test may be used to identify ingredients that inhibit the Elastase Pathway, other tests may be suitable and this invention is not limited to one specific test. Any other test that is known in the art either now or hereafter and which accurately predicts the Elastase Inhibition activity of an ingredient may also be used to identify and select suitable ingredients that inhibit the Elastase Pathway.

A number of ingredients are suitable inhibitors of the Elastase Pathway including *Boswellia Serratia* extract, winter begonia extract, oleanolic acid, ursolic acid, phytocohesin, *Pygeum Africanum* extract, *Padina Pavonica* extract, CP7 PC16, *Actina Boswellia* extract, ligustrum, dipalmitoyl hydroxyproline (sold under the tradename Sepilift DPHP by Seppic), Soft *Pygeurm* extract, chaga mushroom, 7-DHC (7-dehydrocholesterol), white birch extract, polyphenon E, jojoba protein isolate, red raspberry powder, heather extract, hesperitin, hibiscin, Preregen® (mixture of soybean protein and oxido reductases), grapeseed extract, Rusperin C®, (a mixture of butcher's broom extract and heperidin methyl chalcone), hesperidin, caffeine, Pronalen® (a protein hydrolysate obtained from extracted organic germinated wheat seeds) hesperitin, Elhibin® (glycine soja protein), jojoba oil, Phytessence Olive® (a mixture of butylene glycol, water and *Olea Europaea* fruit extract).

F. Histamine Pathway

The Histamine Pathway is the pathway where the amino acid histidine is decarboxylated to form histamine—a reaction that occurs in response to immune challenge or other injury to tissue or skin. The Histamine Pathway Inhibitors may be present in amounts ranging from about 0.0001 to 75%, preferably from about 0.0005 to 70%, more preferably from about 0.001 to 20%.

A test that may be conducted to determine whether an ingredient inhibits the Histamine Pathway may be performed by first growing cells from the rat basophil leukemia (RBL) cell line in Dulbecco's Modification of Eagle Medium (DMEM) with 10% heat activated fetal calf serum (FCS) and seeding in 24 well plates at $2.5 \times 10^5$ cells/well. The cells are grown overnight and treated the next day. Reagents are prepared in DMSO with complete solubilization, specifically: epigallocatechin gallate (EGCG) (100 mM); chrysin (10 mM); apigenin (10 mM); phloridizin (10 mM); curcumin (orange) (10 mM); and gallic acid (10 mM). Chrysin is used as a positive control. Prior to treating the RBL cells, the overnight culture media is removed and the cells washed with phosphate buffered saline (PBS) and equilibrated with PIPES buffer, pH 7.2. (PIPES buffer contains 100 mM NaCl, 5 mM KCl, 0.4 mM $MgCl_2$, 1 mM $CaCl_2$ and 5.6 mM D-glucose. PIPES buffer is known to reduce spontaneous release of histamine). Potential inhibitors of histamine release are added directly to the PIPES buffer (37° C.) and incubated for 30 minutes. Cells were exposed to 100 mM, 10 mM, 1 mM and 0.1 mM doses of the inhibitors. Histamine release was induced by the calcium-ionophore, A23187 (2 mM final) (Sigma C7522). The supernatant was harvested after 30 minutes of exposure to the ionophore and assayed using a Histamine ELISA kit from IBL (distributed by Research Diagnostics). The Histamine ELISA was performed as outlined in the protocol supplied by the manufacturer and the results calculated from the standard curve.

While the above test is suitable for ascertaining which selected ingredients inhibit the Histamine Pathway, other tests, either now known or hereafter developed may be suitable so long as they accurately identify ingredients that are capable of inhibiting the Histamine Pathway.

Ingredients that are known to inhibit the Histamine Pathway include botanicals such as apigenin which is a flavone that may be extracted from celery, parsley, or citrus fruits such as grapefruit peel extract; amentoflavone (which may be isolated from *Selaginella Tamariscina*; luteolin, a flavinoid;

phloretin, or 2',4',6',4-Tetrahydroxydihydrochalcone; grapeseed extract, *Rosmarinus Officinalis* extract, or mixtures of such materials.

G. Histamine Receptor Pathway

The Histamine Receptor Pathway refers to a pathway by which cellular receptors for histamine are activated to bind to histamine, which in turn contributes to the inflammatory condition of tissues or skin. The Histamine Receptor Pathway Inhibitors may be present in amounts ranging from 0.0001 to 75%, preferably from about 0.0005 to 70%, more preferably from about 0.001 to 20%.

A test that may be conducted to determine whether an ingredient inhibits the Histamine Receptor Pathway is performed by radio ligand binding assay. Cellular membranes from recombinant Chinese hamster ovary cell lines are transfected with human H1 receptor cells. Test material at concentrations ranging from 1000 µM to 1 µM are pre-incubated with the cellular membranes. The reaction is initiated by addition of radioactively labeled guanosine 5'-tri phosphate that is unable to be metabolized [$^{35}$S]GTPγS and incubated for an additional 30 minutes at 30° C. When histamine binds to the H1 receptor on the cell membranes, a conformational change occurs in the alpha G protein subunit that is also present on the cell membranes in this assay allowing the [$^{35}$S]GTPγS to bind to the G protein subunit. It is the presence of this bound radioactive ligand that is monitored. If the test compound in the presence of histamine reduces [35S]GTPgS binding by the alpha G protein by 50 percent or more, this indicates receptor antagonist activity.

While the above test is suitable for ascertaining which selected ingredients inhibit the Histamine Receptor Pathway, other tests, either now known or hereafter developed may be suitable so long as they accurately identify ingredients that are capable of inhibiting the Histamine Receptor Pathway.

Suitable Histamine Receptor Pathway Inhibitors include Xanomax® (a high potency extract of Mangosteen), Japanese Butterbur, *Garcinia Mangostana* Peel Extract (sold under the tradename Xanomax 40% by Amax Nutrasource, Inc.), and mixtures thereof.

H. LO Pathway

The LO Pathway means the pathway by which the enzyme lipooxygenase, preferably 5-lipooxygenase, catalyzes the conversion of arachidonic acid to 5-hydroperoxyeicosatetraenoic acid and then to leukotriene A4, which ultimately contributes to inflammation or pain in immune challenged tissue such as skin. The LO Pathway Inhibitors may be present in amounts ranging from about 0.0001 to 75%, preferably from about 0.0005 to 70%, more preferably from about 0.001 to 20%.

A simple test that can be used to determine whether an ingredient is able to inhibit the LO Pathway is performed by slightly modifying the procedure in a kit—The Lipoxygenase Inhibitor Screening Assay Kit from Cayman Chemical (760700)—but where the 15-Lipooxygenase that is found in the kit is substituted with 5-LO (also purchased from Cayman Chemical, 60401). The 5-LO is diluted to 225 U/ml in 0.1M Tris-HCl (pH 7.4) and 90 µl (20 U) are added to each well of a 96 well plate. Caffeic acid is used as a control and added to the well at a final concentration of 300 µg/ml. The test samples are usually tested at final concentrations of 1, 10, 100 and 1000 µg/ml. Upon addition of the enzyme and test sample, the contents of the wells are mixed and incubated for 5 minutes. The enzymatic reaction is initiated with the addition of linoleic acid (substrate) at a final concentration of 100 µM in the wells. The plate is then placed on an orbital shaker for 5 minutes. After the 5 minute reaction time, a chromogen is then added to each well and allowed to react for 10 minutes. The chromogen reacts with the hydro-peroxides produced as a result of the lipoxygenation reaction and also acts to stop the reaction. The resulting "color" is read on the plate reader at 500 nm. The absorbance at 500 nm is proportional to the level of 5-LO activity. The percent inhibition is then calculated based on the absorbance in the presence and absence of the inhibitor.

While the above test is suitable for ascertaining which selected ingredients inhibit the 5-LO Pathway, other tests, either now known or hereafter developed may be suitable so long as they accurately identify ingredients that are capable of inhibiting the 5-LO Pathway.

Suitable LO Pathway Inhibitors include *Haplophyllum hispanicum* Spach, *Scutellaria Rivularis* extracts and its active components, alpha ketoboswellic acid, Zileuton® (1-(1-benzothiophen-2-ylethyl)-1-hydroxy-urea), *Centaurium* extract, nordihydroguaiaretic acid, ginger oil, resveratrol, *Polygonum Cuspidatum* extract, cedar himalaya extract, tetrahydrocurcuminoids, *Nigella Sativa* essential oil, copaiba balsam, Australian sandalwood, *Rhodiola Rosea*, frankincense, blue cypress oil, blue chamomile oil, anti-inflammatory oil blend, vetiver mada, bulgarian rose oil, Helichrysum oil, rosmarinic acid, resveratrol triphosphate, noni leaf extract, and mixtures thereof.

I. PDE Pathway

The PDE Pathway means that pathway by which PDE (phosphodiesterase) including phosphodiesterase-4 cleaves the phosphodiester bond that may be found in proteins and other molecules present in bacteria, viruses, and other molecules that contribute to skin inflammation.

A test for determining whether an ingredient inhibits the PDE Pathway may be performed using a radionuclide assay using [3H] cAMP as a substrate. The test procedure utilizes purified cAMP dependent phosphodiesterase (PDE4). All test materials are suspended or dissolved in 1% DMSO. The test materials (at concentrations ranging from 0.001 to 1000 µg/ml) are incubated with the purified PDE4 enzyme for 20 minutes before determining the amount of [$^3$H] adenosine generated. Upon incubation, the PDE4 enzyme will convert the [3H] cAMP to [$^3$H] adenosine which is then measured via scintillation counter. IBMX (isobutylmethylxanthine) was used as the positive control inhibitor (at 4.35 µg/ml).

While the above test is suitable for ascertaining which selected ingredients inhibit the PDE Pathway, other tests, either now known or hereafter developed may be suitable so long as they accurately identify ingredients that are capable of inhibiting the PDE Pathway.

Examples of PDE Pathway Inhibitors include nordihydroguaiaretic acid, emodin (an extract from Rheum Emodi or rhubarb), 18-B-glycerrhetinic acid, caffeine, wild yam powder, *Anemarrhena asphodeloides* or *Zhi Mu* extract, *Eucomia* extract, *Uncaria Tomentosa* (also referred to as C-med 100), or mixtures thereof.

J. PLA Pathway

The term PLA Pathway means the pathway by which PLA-2 (the phospholipase A2 enzyme) hydrolyzes phospholipids to form fatty acid lysophospholipid products such as arachidonic acid, which ultimately converts to leukotrienes and prostaglandins and contributes to the inflammatory response in immune challenged tissue such as skin. PLA Pathway Inhibitors may be present from about 0.0001 to 75%, preferably from about 0.0005 to 70%, more preferably from about 0.001 to 20%.

A test that determines whether an ingredient has PLA Pathway inhibiting properties may be conducted by preparing a stock solution of substrate, 2-(6-(7-nitrobenz-2-oxa-1,3-diaazol-4-yl)amino)-hexanoyl-1-hexadecanoyl-sn-glycero- 3-phosphocholine (NBDC6-HPC sold by Molecular Probes) (1 mM in EtOH) diluted 1:100 in D-PBS. The final concentration of substrate is 0.001 mM as the assay dilutes all components 10 fold. The positive control, thioetheramide (Cayman, 62750), is tested at a final concentration of 5 µM. The samples to be tested are tested at a final concentration of 0.001%, 0.01%, 0.1% and 1% [v/v] or at 1, 10, 100 and 1000 µg/ml in D-PBS. The PLA2 enzyme used is the secretory PLA2 human enzyme Type V (Cayman 10004913). The enzyme final concentration tested is a 1:1000 dilution of the supplied vial. The reaction proceeded in 200 µl total solution initiated by addition of enzyme. Fluorescence is read immediately and subsequently each minute for a total of 8 minutes. (Excitation 470 nm Emission 540 nm). The fluorescence readings for each sample are plotted versus time and the initial reaction velocity is calculated from the initial slope of the fluorescence versus time for each inhibitor concentration. The initial reaction velocity is plotted as a function of the end concentration of the potential inhibitor and the $IC_{50}$ is then calculated. The $IC_{50}$ corresponds to the concentration of inhibitor that results in a 50% reduction of the initial reaction velocity in the absence of the inhibitor.

While the above test is suitable for ascertaining which selected ingredients inhibit the PLA Pathway, other tests, either now known or hereafter developed may be suitable so long as they accurately identify ingredients that are capable of inhibiting the PLA Pathway.

Ingredients that are suitable for inhibiting the PLA Pathway include botanicals such as *Lyngbya* extract, grapeseed extract, amentoflavone, Licochalcone, polypore, *Viapure Poria* extract, *Polyporus Umbellatus*, Avocado extract, *Camella Sinensis* extract, Chrysanthellum Indicum, *Tridentata marginate* extract (also referred to as tridentatol C), pomegranate extract, ellagic acid, paeoniflorin PR-3 (an extract of *Paeonia Albiflora Pall*) hesperitin, green tea polyphenols, Gorgonian extract, and mixtures thereof.

K. VEGF Pathway

The VEGF Pathway means the pathway by which VEGF (vascular endothelial growth factor) causes angiogensis (the formation of blood vessels) in immune challenged or damaged skin or tissue. The VEGF Pathway Inhibitors may be present in amounts ranging from 0.0001 to 75%, preferably from about 0.0005 to 70%, more preferably from about 0.001 to 20%.

A test that is suitable for determining whether a particular ingredient inhibits the VEGF Pathway is based upon the analysis of the ability of the test material to inhibit the synthesis and release of VEGF from Normal Human Epidermal Keratinocytes that have been stimulated with either tumor necrosis factor a (TNFa), or UVA or UVB rays.

Normal Human Epidermal Keratinocytes (Cascade Biologics) are seeded and grown to subconfluence in 6 well plates. Upon reaching subconfluence, the EGF and Bovine Pituitary Extract (BPE) are removed from the media and the test materials tested at final concentrations of 0.0001, 0.001, 0.01, 0.1 and 1 mg/ml for powdered samples or at 0.001%, 0.01%, 0.1% or 1% (v/v) for liquid samples. After incubating for 48 hours, the cells are stimulated with either TNFa (50 ng/ml from R&D Systems), UVA (10 $J/m^2$, F20T12-BLB bulbs) or UVB (20 $mJ/cm^2$, FS40 bulbs) and incubated for an additional 24 hours in the presence of the test material. At the conclusion of the 24 hour incubation, supernatants are harvested and VEGF levels are measured via an ELISA technique (R&D Systems). The VEGF ELISA was performed as outlined in the protocol supplied by the manufacturer and the results calculated from the standard curve.

While the above test is suitable for ascertaining which selected ingredients inhibit the VEGF Pathway, other tests, either now known or hereafter developed may be suitable so long as they accurately identify ingredients that are capable of inhibiting the VEGF Pathway.

Suitable VEGF Pathway Inhibitors include extracts from the *Saussurea* genus such as *Saussurea Costus* exract, *Saussurea Lappa*, Sesquiterpene lactones, magnolia extract, Biobenefity® (a mixture of butylene glycol, water, and *Cynara Scolymus* (Artichoke) Leaf Extract), hypoestoxide (HE); and *Magnolia Officianalis* Bark extract, *Echineacea Pallida* extract, and mixtures thereof.

In the method of the invention a plurality of Pathways are identified and ingredients that have an inhibitory effect on the Pathways identified are selected by performing the tests mentioned herein or similar tests that predict the efficacy of the selected material in inhibiting the pathway of interest. The active materials are then incorporated into a composition suitable for topical application. Two, three, four, five, six, seven, eight, nine, ten, or all eleven Pathways may be identified and the corresponding inhibitory ingredients for each of the Pathways identified are formulated into the topical composition.

For example, it is believed that dark under eye circles, one feature of skin that is not normalized, may be caused by inflammatory reactions involving one or more of the Pathways mentioned herein. In that case, the Pathways that contribute to the type of inflammation or irritation that produces dark under eye circles are identified, then the particular ingredients that inhibit the Pathways identified are selected. The selected ingredients are formulated into a topical composition that can be applied to the affected area one or more times per day to treat the condition.

In another example, skin that has been sunburned is red, painful, and warm. A Plurality of the Pathways are identified, ingredients are selected that inhibit the identified Pathways, and the ingredients are formulated into a topical composition for use in treating the sunburned skin.

In yet another example, certain irritated conditions contribute to aged skin. For example, sallow pigmentation or age spots may be due in part to inflammatory conditions. In this case the Pathways that contribute to the sallow pigmentation or age spots are identified, ingredients are selected that inhibit the Pathways identified, and those ingredients are formulated into a topical composition for application to treat the sallow pigmentation or age spots.

The invention also comprises a method for treating irritated or inflamed skin, or skin that is no longer normalized, by identifying a plurality of Pathways that contribute to inflammation, selecting ingredients that inhibit the Pathways identified, and formulating those ingredients into a topical composition for application to skin to treat the condition.

The topical compositions may be in the form of creams, lotions, sprays, mousses, toners, soaps, color cosmetic products, and so on. They may be applied once, twice, or more times per day. They may be applied in regimens, or as part of a regimen. For example, in the morning the user may cleanse and tone the skin and apply the composition prepared according to the invention. Then in the evening prior to retiring the user may again cleanse and tone the skin and apply the composition as a night cream. The Pathway inhibitory ingredients may be found in all steps of the regimen or only one. For example, the Pathway inhibitory ingredients may be found in the cleanser, toner, and skin cream or lotion. Alternatively, the Pathway inhibitory ingredients may be found only in the toner and skin cream, or skin cream alone. The Pathway inhibitory ingredients may also be formulated into color cosmetics such as foundations, blush, concealer, eye shadow, lipstick, and so on.

III. The Compositions

The compositions used in the methods of the invention may comprise a variety of other ingredients. The compositions may be found in the anhydrous, emulsion, gel, solution, or suspension form. If present in the solution or gel form, from about 0.01-99%, preferably from about 0.5-95%, more preferably from about 1-90% by weight of the total composition of water may be present. If present in the emulsion form, water-in-oil or oil-in-water emulsions may be appropriate, in which case in addition to the amounts of water already mentioned, the compositions may contain from about 0.01-98%, preferably from about 0.1-95%, more preferably from about 0.5-90% by weight of the total composition of oil. The composition may contain a variety of other ingredients including but not limited to those set forth herein. If present in the solution or gel form, the composition may comprise from about 0.01-99% water and other optional ingredients. If present in the anhydrous form, the composition may contain waxes, oils, or humectants in the amounts set forth herein.

A. Volatile Oils

1. Volatile Silicones

Suitable volatile oils that may be used in the compositions of the invention generally have a viscosity ranging from about 0.5 to 5 centistokes 25° C. and include linear silicones, cyclic silicones, branched silicones, paraffinic hydrocarbons, or mixtures thereof.

Cyclic silicones are of the general formula:

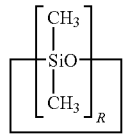

where n=3-6.

Linear volatile silicones in accordance with the invention have the general formula:

$(CH_3)_3Si\text{—}O\text{—}[Si(CH_3)_2\text{—}O]_n\text{—}Si(CH_3)_3$ where n=0, 1, 2, 3, 4, or 5, preferably 0, 1, 2, 3, or 4.

Branched volatile silicones are generally of the formula:

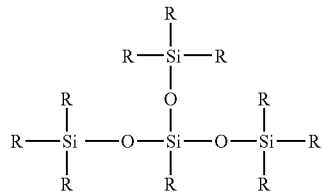

wherein R is $C_{1-4}$ alkyl, preferably methyl.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, dodecamethylcyclohexasiloxane and the like. Also suitable are linear volatile silicones such as hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof.

Suitable branched volatile silicones include methyl trimethicone, ethyl trimethicone, propyl trimethicone, butyl trimethicone and the like. Methyl trimethicone may be purchased from Shin-Etsu Silicones and has the trade name TMF 1.5, having the viscosity of 1.5 centistokes at 25° C.

2. Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference in their entireties for all purposes.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

B. Non-Volatile Oils

A variety of nonvolatile oils are also suitable for use in the cosmetic compositions of the invention. The nonvolatile oils generally have a viscosity of greater than about 5 to 10 centistokes at 25° C., and may range in viscosity up to about 1,000,000 centipoise at 25° C. Preferably, the nonvolatile oils are liquid. Further examples of nonvolatile oils include, but are not limited to:

1. Esters

Suitable esters are mono-, di-, and triesters. The composition may comprise one or more esters selected from the group, or mixtures thereof.

(a) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(b). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisostearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(c). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described on pages 2679-2688 of Volume 3 of the C.T.F.A. Cosmetic Ingredient Dictionary and Handbook, Eleventh Edition, 2006, which is hereby incorporated by reference in its entirety.

2. Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

3. Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisostearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

4. Nonvolatile Silicones

Nonvolatile silicone oils, both water soluble and water insoluble, are also suitable for use in the composition. Such silicones preferably have a viscosity ranging from about 10 to 800,000 cst, preferably 20 to 200,000 cst at 25° C. Suitable water insoluble silicones include amine functional silicones such as amodimethicone; phenyl substituted silicones such as bisphenylhexamethicone, trimethylsiloxyphenyl dimethicone, phenyl trimethicone, or polyphenylmethylsiloxane; dimethicone, dimethicone substituted with $C_{2-30}$ alkyl groups such cetyl dimethicone.

Nonvolatile silicones may have the following general formula:

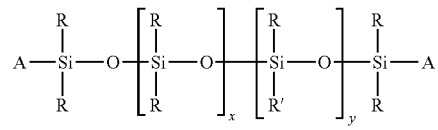

wherein R and R' are each independently $C_{1-30}$ straight or branched chain, saturated or unsaturated alkyl, phenyl or aryl, trialkylsiloxy, and x and y are each independently 0-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the tradenames Abil Wax 9801, or 9814.

C. Surfactants

The composition of the invention may contain one or more surfactants. The surfactants may be silicone or organic surfactants.

1. Silicone Surfactants

Suitable silicone surfactants include polyorganosiloxane polymers that have amphiphilic properties, for example contain both hydrophilic radicals and lipophilic radicals. These silicone surfactants may be liquids or solids at room temperature and include, but are not limited to those set forth herein.

(a). Dimethicone Copolyols or Alkyl Dimethicone Copolyols

One type of silicone surfactant that may be used is generally referred to as dimethicone copolyol or alkyl dimethicone copolyol. This surfactant is either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

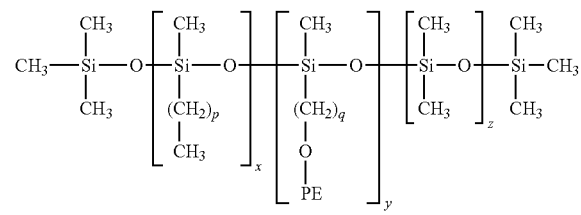

wherein p and q are from 0 to 40 (the range including all numbers between and sub-ranges such as 2, 3, 4, 13, 14, 15, 16, 17, 18, etc.), and PE is $(-C_2H_4O)_a-(-C_3H_6O)_b-H$, wherein a is from 0 to 25, b is from 0 to 25, with the proviso that a and b cannot both be 0 simultaneously, wherein x, y and z are each independently ranging from 0 to 1 million, with the proviso that they cannot all be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

(b). Crosslinked Silicone Surfactants

Also suitable are various types of crosslinked silicone surfactants are referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organo-polysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986 and U.S. Pat. No. 5,412,004, U.S. Pat. No. 5,837,793 and U.S. Pat. No. 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer.

2. Organic Surfactants

The composition may contain one or more additional surfactants, such as nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are formed by the reaction of a carboxylic acid with an alkylene oxide or with a polymeric ether. The resulting products have the general formula: where RCO is the carboxylic ester radical, X is hydrogen or lower alkyl, and n is the number of polymerized alkoxy groups. In the case of the diesters, the two RCO-groups do not need to be identical. Preferably, R is a $C_{6-30}$ straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula: wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with $C_{6-30}$, preferably $C_{12-22}$ fatty acids. Examples of such ingredients include Polysorbates 20-85, sorbitan oleate, sorbitan sesquioleate, sorbitan palmitate, sorbitan sesquiisostearate, sorbitan stearate, and so on.

Certain types of amphoteric, zwitterionic, or cationic surfactants may also be used in the compositions. Descriptions of such surfactants are set forth in U.S. Pat. No. 5,843,193, which is hereby incorporated by reference in its entirety.

D. Oil Phase Structuring Agents

If desired, the composition may contain one or more oil phase structuring agents in the oil phase of the emulsion or anhydrous composition. The term "oil phase structuring agent" means an ingredient or combination of ingredients, soluble or dispersible in the oil phase, which will increase the viscosity, or structure, the oil phase. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition. Suitable oil phase structuring agents include those that are silicone based or organic based. They may be polymers or non-polymers, synthetic, natural, or a combination of both.

1. Silicone Structuring Agents

A variety of oil phase structuring agents may be silicone based, such as silicone elastomers, silicone gums, silicone waxes, linear silicones having a degree of polymerization that provides the silicone with a degree of viscosity such that when incorporated into the cosmetic composition it is capable of increasing the viscosity of the oil phase. Examples of silicone structuring agents include, but are not limited to:

(a). Silicone Elastomers

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or nonvolatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crossopolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety.

(b). Silicone Gums

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

The silicone gums that are used in the compositions include, but are not limited to, those of the general formula wherein:

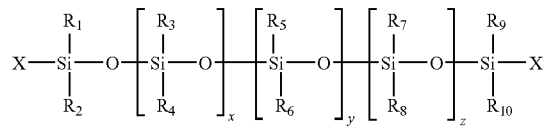

$R_1$ to $R_9$ are each independently an alkyl having 1 to 30 carbon atoms, aryl, or aralkyl; and X is OH or a $C_{1-30}$ alkyl, or vinyl; and wherein x, y, or z may be zero with the proviso that no more than two of x, y, or z are zero at any one time, and further that x, y, and z are such that the silicone gum has a viscosity of at least about 500,000 cst, ranging up to about 100 million centistokes at 25° C. Preferred is where R is methyl or OH.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

(c). Silicone Waxes

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

2. Polyamides or Silicone Polyamides

Also suitable as oil phase structuring agents are various types of polymeric compounds such as polyamides or silicone polyamides.

The term silicone polyamide means a polymer comprised of silicone monomers and monomers containing amide groups as further described herein. The silicone polyamide preferably comprises moieties of the general formula:

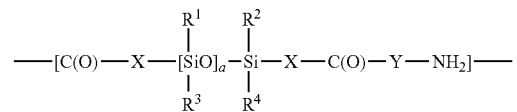

where X is a linear or branched alkylene having from about 1-30 carbon atoms; $R_1$, $R_2$, $R_3$, and $R_4$ are each independently $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

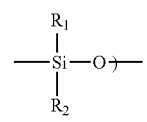

and Y is:

(a) a linear or branched alkylene having from about 1-40 carbon atoms which may be substituted with (i) one or more amide groups having the general formula $R_1 CONR_1$, or (ii) $C_{5-6}$ cyclic ring, or (iii) phenylene which may be substituted with one or more $C_{1-10}$ alkyl groups, or (iv) hydroxy, or (v)

$C_{3-8}$ cycloalkane, or (vi) $C_{1-20}$ alkyl which may be substituted with one or more hydroxy groups, or (vii) $C_{1-10}$ alkyl amines; or (b) $TR_5R_6R_7$ wherein $R_5$, $R_6$, and $R_7$, are each independently a $C_{1-10}$ linear or branched alkylenes, and T is $CR_8$ wherein $R_8$ is hydrogen, a trivalent atom N, P, or Al, or a $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

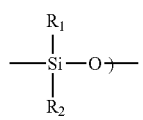

Preferred is where $R_1$, $R_2$, $R_3$, and $R_4$ are $C_{1-10}$, preferably methyl; and X and Y is a linear or branched alkylene. Preferred are silicone polyamides having the general formula

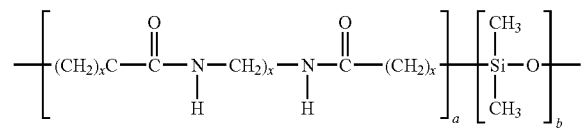

wherein a and b are each independently sufficient to provide a silicone polyamide polymer having a melting point ranging from about 60 to 120° C., and a molecular weight ranging from about 40,000 to 500,000 Daltons. One type of silicone polyamide that may be used in the compositions of the invention may be purchased from Dow Corning Corporation under the tradename Dow Corning 2-8178 gellant which has the CTFA name nylon-611/dimethicone copolymer which is sold in a composition containing PPG-3 myristyl ether.

Also suitable are polyamides such as those purchased from Arizona Chemical under the tradenames Uniclear and Sylvaclear. Such polyamides may be ester terminated or amide terminated. Examples of ester terminated polyamides include, but are not limited to those having the general formula:

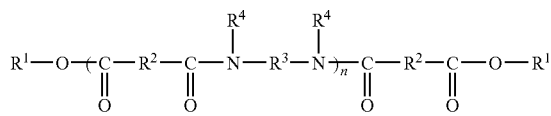

wherein n denotes a number of amide units such that the number of ester groups ranges from about 10% to 50% of the total number of ester and amide groups; each $R^1$ is independently an alkyl or alkenyl group containing at least 4 carbon atoms; each $R^2$ is independently a $C_{4-42}$ hydrocarbon group, with the proviso that at least 50% of the $R^2$ groups are a C30-42 hydrocarbon; each $R^3$ is independently an organic group containing at least 2 carbon atoms, hydrogen atoms and optionally one or more oxygen or nitrogen atoms; and each $R^4$ is independently a hydrogen atom, a $C_{1-10}$ alkyl group or a direct bond to $R^3$ or to another $R^4$, such that the nitrogen atom to which $R^3$ and $R^4$ are both attached forms part of a heterocyclic structure defined by $R_4$—N—$R_3$, with at least 50% of the groups $R_4$ representing a hydrogen atom.

General examples of ester and amide terminated polyamides that may be used as oil phase gelling agents include those sold by Arizona Chemical under the tradenames Sylvaclear A200V or A2614V, both having the CTFA name ethylenediamine/hydrogenated dimer dilinoleate copolymer/bis-di-$C_{14-18}$ alkyl amide; Sylvaclear AF1900V; Sylvaclear C75V having the CTFA name bis-stearyl ethylenediamine/neopentyl glycol/stearyl hydrogenated dimer dilinoleate copolymer; Sylvaclear PA1200V having the CTFA name Polyamide-3; Sylvaclear PE400V; Sylvaclear WF1500V; or Uniclear, such as Uniclear 100VG having the INCI name ethylenediamine/stearyl dimer dilinoleate copolymer; or ethylenediamine/stearyl dimer ditallate copolymer. Other examples of suitable polyamides include those sold by Henkel under the Versamid trademark (such as Versamid 930, 744, 1655), or by Olin Mathieson Chemical Corp. under the brand name Onamid S or Onamid C.

3. Natural or Synthetic Organic Waxes

Also suitable as the oil phase structuring agent may be one or more natural or synthetic waxes such as animal, vegetable, or mineral waxes. Preferably such waxes will have a higher melting point such as from about 60 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, oleic acid, stearic acid, and so on.

4. Montmorillonite Minerals

One type of structuring agent that may be used in the composition comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

5. Silicas and Silicates

Another type of structuring agent that may be used in the oil phase of the composition is silica, silicates, or silica silylate, and alkali metal or alkaline earth metal derivatives thereof. These silicas and silicates are generally found in the particulate form and include silica, silica silylate, magnesium aluminum silicate, and the like.

E. Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols in monomeric or polymeric form such as polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, ethylhexylglycerin, trehalose, trehalose dihydrdate, and the like. Preferably, the humectants used in the composition of the invention are $C_{1-6}$, preferably $C_{2-4}$ alkylene glycols, most particularly butylene glycol.

F. Aqueous Phase Structuring Agents

If the compositions of the invention contain an aqueous phase it may be desirable to include one or more aqueous phase structuring agents in the composition. Such agents will typically thicken or increase the viscosity of the aqueous phase. If present, suggested ranges are from about 0.01 to 30%, preferably from about 0.1 to 20%, more preferably from about 0.5 to 15% by weight of the total composition. Examples of such agents include various acrylate based thickening agents, natural or synthetic gums, and the like.

1. Acrylate Polymers

For example, acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymer of A, B, and C monomers wherein A and B are as defined above, and C has the general formula:

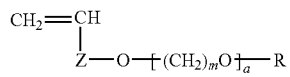

wherein Z is —$(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

in which R' denotes H or $CH_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl(meth)acrylate, divinylbenzene, (poly)ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 alkyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames.

Particularly suitable as the aqueous phase thickening agent are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

2. High Molecular Weight PEG or Polyglycerins

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

3. Polysaccharides

Also suitable as aqueous phase thickening agents are various types of polysaccharides, such as xanthan gum, cellulose, dextrin, cyclodextrin, hydroxyethylcellulose, acacia gum, and the like.

G. Botanical Extracts

It may be desirable to include one or more botanical extracts in the compositions in addition to those botanical extracts that have kinase inhibitor activity. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, padica pavonica extract, thermus thermophilis ferment extract, camelina sativa seed oil, boswellia serrata extract, olive extract, aribodopsis thaliana extract, acacia dealbata extract, acer saccharinum (sugar maple), acidopholus, acorns, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, rosemary, poppy, and the like. Further specific examples include, but are not limited to, *Glycyrrhiza Glabra, Salix Nigra, Macrocycstis Pyrifera, Pyrus Malus, Saxifraga Sarmentosa, Vilis Vinifera, Moms Nigra, Scutellaria Baicalensis, Anthemis Nobilis, Salvia Sclarea, Citrus Medica Limonum, Panax Ginseng*, and mixtures thereof.

H. Particulate Materials

The compositions of the invention may contain particulate materials in the form of pigments, inert particulates, or mixtures thereof. If present, suggested ranges are from about 0.1-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

1. Powders

The particulate matter may be colored or non-colored (for example white) non-pigmentatious powders. Suitable non-pigmentatious powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

2. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

I. Preservatives

The composition may contain 0.001-8%, preferably 0.01-6%, more preferably 0.05-5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the like. In one preferred embodiment the composition is free of parabens.

J. Vitamins and Antioxidants

The compositions of the invention, may contain vitamins and/or coenzymes, as well as antioxidants. If so, 0.001-10%, preferably 0.01-8%, more preferably 0.05-5% by weight of the total composition are suggested. Suitable vitamins include ascorbic acid and derivatives thereof, the B vitamins such as thiamine, riboflavin, pyridoxin, panthenol, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

K. Film Forming Polymers

In certain cases it is desirable to include film forming polymers in the compositions of the invention. If present, the polymers may range from about 0.01 to 85%, preferably from about 0.1 to 75%, preferably from about 0.5 to 40% by weight of the total compositions. Such polymers may silicones, copolymers of silicones and organic groups, or polymers or copolymers containing entirely organic groups. Examples of organic monomers that may be used to construct suitable film forming polymers include styrene, vinyl pyrrolidone, acrylic or methacrylic acid or its $C_{1-10}$ simple esters such as methyl methacrylate, methylacrylate, ethyl methacrylate, ethylacrylate, butyl acrylate, butyl methacrylate, and so on. The organic monomers may be neutralized with sales such as ammonia, sodium, potassium, and the like (e.g. ammonium acrylate, ammonium methacrylate, sodium acrylate, sodium methacrylate, and the like). The organic monomers may be copolymerized with other organic ingredients such as glycols, fatty acids, esters like those mentioned herein. Suitable film forming polymers also include copolymers of organic monomers and silicone, including a class of polymers generally referred to as silicone acrylate copolymers. One example of such polymers includes polydimethylsiloxane-g-polyacrylates sold by 3M Company under the tradename VS-70. Also suitable are silicone film forming polymers, including a group of silicones referred as silicone resins (trimethylsiloxysilicate or polymethylsilsesquioxane). A variety of film forming polymers may be used in the compositions of the invention depending on the desired end benefit.

The invention will be further described in connection with the following examples which are set forth for the purposes of illustration only.

EXAMPLE 1

Ingredients were selected that had inhibitory activity for each of the 11 Pathways mentioned above were selected using the test methods set forth herein, and combined to form an ingredient mixture as follows:

| Ingredient | Pathway Inhibited | % by weight |
|---|---|---|
| Grapefruit Peel extract | Histamine Pathway | 0.10 |
| Gorgonian Extract | PLA-1 Pathway | 0.50 |
| Nordihydroguaiaretic Acid | 5-LO Pathway | 0.02 |
| Resveratrol | COX-2 Pathway | 0.10 |
| Fucoidan YSK (*Cladosiphon Okamuranus* extract) | Chemotaxis Pathway | 0.10 |
| Polysea PF (Algae extract) | Adhesion Pathway | 0.50 |
| *Siegesbeckia Orientalis* | Collagenase Pathway | 0.20 |
| White Birch extract | Elastase Pathway | 0.10 |
| 18-B-glycerrhetinic acid | PDE Pathway | 0.10 |
| Magnolia extract | VEGF Pathway | 0.05 |
| Mangostin or *Garcinia Mangostana* Peel extract (Xanomax ®) | Histamine Receptor Pathway | 0.10 |

EXAMPLE 2

Various compositions containing the combination in Example 1 were tested for ability to inhibit or curtail skin inflammation. The test compositions were prepared as follows:

| Ingredient | Formula 7666/4 New Mag | Formula 7666/3P | Formula 7666/1 Old | Formula 7666/3 New |
|---|---|---|---|---|
| | % by weight | | | |
| Hydrogenated lecithin | 1.00 | 1.00 | — | 1.00 |
| NDGA[1] | 0.02 | — | 0.50 | 0.02 |
| *Magnolia Officianalis* Bark Extract[2] | 0.05 | — | 0.05 | 0.05 |
| Butylene glycol/*Gorgonian* (Sea Whip) extract[3] | 0.50 | — | 0.50 | 0.50 |
| BHT | — | — | 0.05 | — |
| Ammonium acrylodimethyl-taurate copolymer | 1.00 | 1.00 | 1.00 | 1.00 |
| Squalane | 3.00 | 0.018 | 3.00 | 3.00 |
| Glycyrrhetinic acid[4] | 0.10 | — | 0.10 | 0.10 |
| Phenoxyethanol | 0.52 | 0.03 | 0.048 | 0.52 |
| Disodium EDTA | 0.10 | — | 0.10 | 0.10 |
| Cetyl alcohol | 0.50 | 0.50 | 0.50 | 0.50 |
| *Cladosiphon Okamuranus* extract/dextrin (Fucoidan YSK)[4] | 0.50 | — | 0.10 | 0.10 |
| Algae extract (Polysea PF)[5] | 0.50 | — | 0.50 | 0.50 |
| Dimethicone | 1.00 | 1.00 | — | 1.00 |
| Dimethicone/dimethiconol | — | — | 1.00 | — |
| Cetearyl alcohol | 1.00 | 1.00 | 1.00 | 1.00 |
| Butylene glycol | 9.00 | 9.00 | 9.00 | 9.00 |
| *Garcinia Mangostana* Peel extract (Mangostin)[6] | 0.10 | — | 0.10 | 0.10 |
| Caprylyl glycol/phenoxy-ethanol/hexylene glycol | 1.00 | 1.00 | 1.00 | 1.00 |
| Xanthan gum | 0.20 | 0.20 | 0.20 | 0.20 |
| Cetearyl alcohol/Cetearyl glucoside | 3.00 | 3.00 | 3.00 | 3.00 |
| Tromethane | 0.20 | 0.20 | 0.20 | 0.20 |
| Carbomer | 0.20 | 0.20 | 0.20 | 0.20 |
| PEG-6 | 4.00 | 4.00 | 4.00 | 4.00 |
| Polyglyceryl-3 beeswax | 0.50 | 0.50 | — | 0.50 |
| Behenyl alcohol | 1.00 | 1.00 | 1.00 | 1.00 |
| Isostearyl neopentanoate | 3.00 | 3.00 | 3.00 | 3.00 |
| Hyaluronic acid powder - sodium salt | 0.02 | 0.02 | 0.02 | 0.02 |
| *Citrus Grandis* (Grapefruit) peel extract[7] | 0.10 | — | 0.10 | 0.10 |
| *Polygonum Cuspidatum* extract (resveratrol)[8] | 0.10 | — | 0.10 | 0.10 |
| Shea butter | 2.00 | 2.00 | 2.00 | 2.00 |
| *Siegesbeckia Orientalis* extract[9] | 0.20 | — | 0.20 | 0.20 |
| *Betula Alba* (White Birch) extract[10] | 0.10 | — | 1.00 | 0.10 |
| Glycerin | 6.00 | 6.00 | 6.00 | 6.00 |
| Water | QS 100 | QS 100 | QS 100 | QS 100 |

[1]Nordihydroguaiaretic acid, a 5-LO Pathway Inhibitor
[2]VEGF Pathway Inhibitor
[3]PLA-1 Pathway Inhibitor. Sea Whip extract is also known as *Gorgonian* extract
[4]PDE Pathway Inhibitor
[5]Fucoidan YSK, a Chemotaxis Pathway Inhibitor
[6]Polysea PF, an Adhesion Pathway Inhibitor
[7]Mangostin, a Histamine Receptor Pathway Inhibitor
[8]Histamine Pathway Inhibitor
[9]COX-2 Pathway Inhibitor
[10]Collagenase Pathway Inhibitor
[11]Elastase Pathway Inhibitor Also tested were:
Cola: Cola nitidia extract in 10% hydroalcoholic solution
Hydrocortisone: 1% hydrocortisone cream purchased from CVS pharmacy.

Seven volunteers with a history of skin sensitivity to Balsam of Peru were chosen for the study. 1.5 inch square areas were marked on the volar forearms of the subjects; with one of the areas corresponding to the untreated control. The test materials were applied on the respective sites and after 20 minutes, Balsam of Peru was applied at the rate of approximately 4 mg/cm2 in a 1.5 cm diameter circle. When redness appeared the Balsam of Peru was wiped off with a wet towel and the degree of redness measured with a Minolta Chromometer. The results are shown in the FIGURE. The "Percent Activity" refers to the activity of each composition in inhibiting inflammation. The Cola Nitidia composition is a known inflammation inhibitor. It is seen that the compositions of the invention (7666/4 New Mag; 7666/1 Old; and 7666/3 New) are significantly more effective in inhibiting inflammation that composition 7666/3P and 1% hydrocortisone cream sold over the counter, the latter being a well known treatment for skin inflammation.

EXAMPLE 3

A skin care lotion according to the invention was prepared as follows:

| Ingredient | w/w % |
|---|---|
| *Garcinia Mangostana* Peel extract (Histamine Receptor Pathway) | 0.10 |
| *Betula Alba* extract (Elastase Pathway) | 0.10 |
| *Citris Grandis* (Grapefruit) Peel extract (Histamine Pathway) | 0.10 |
| Xanthan gum | 0.20 |
| Tromethamine | 0.20 |
| Shea butter | 2.00 |
| *Siegesbeckia Orientalis* extract/glycerin (Collagenase Pathway) | 0.20 |
| Dimethicone | 1.00 |
| *Polygonum Cuspidatum* extract (COX Pathway) | 0.10 |
| Algae extract (Polysea PF) (Adhesion Pathway) | 0.50 |
| Phenoxyethanol | 0.02 |
| PEG-6 | 4.00 |
| Norhydroguaiaretic acid (LO Pathway) | 0.02 |
| Cetearyl alcohol/cetearyl glucoside | 3.00 |
| Hydrogenated lecithin | 1.00 |
| Sodium hyaluronate | 0.02 |
| Butylene glycol/Sea Whip extract | 0.50 |
| Glycerin | 6.00 |
| *Cladosiphon Okamuronus* extract/dextran | 0.10 |
| Squalane | 3.00 |
| Phenoxyethanol | 0.03 |
| Caprylyl glycol/phenoxyethanol/hexylene glycol | 1.00 |
| Disodium EDTA | 0.10 |
| Cetearyl alcohol | 1.00 |
| Water | QS |
| Polyglyceryl-3 beeswax | 0.50 |
| Cetyl alcohol | 0.50 |
| Isostearyl neopentanoate | 3.00 |
| Carbomer (Carbopol 980) | 0.20 |
| Behenyl alcohol | 1.00 |
| Butylene glycol | 9.00 |
| Ammonium acryloyldimethyltaurate/VP copolymer | 1.00 |
| *Magnolia Officianalis* Bark extract (VEGF Pathway) | 0.05 |

The composition was prepared by combining the ingredients and mixing well to form a lotion. The lotion contains selected ingredients that inhibit each of the 11 Pathways as identified herein.

EXAMPLE 4

SPF containing redness relief creams were prepared as follows:

| | w/w % | |
|---|---|---|
| Ingredient | 1 | 2 |
| Cholesterol/potassium sulfate | 0.10 | |
| Wheat (*Triticum Vulgare*) Bran Extract/Olive (*Olea Europaea*) Extract | 0.20 | |
| Laureth-23 | 0.17 | |
| Dimethicone/trisiloxane | | 3.00 |
| Water/ethylhexyl palmitate/butylene glycol/cholesterol/*astrocaryum murmuru* butter/linoleic acid coffee robusta seed extract/ethylhexyl stearate/carbomer/propylene glycol dicaprylate/phytosphingosine (Chemotaxis Pathway Inhibitor) | 1.00 | 1.00 |
| Caprylic/capric/myristic/stearic triglyceride | 3.00 | |
| Ethylhexyl salicylate | 5.00 | 5.00 |
| Aminopropyl ascorbyl phosphate | 0.10 | 0.10 |
| Cholesterol | 0.20 | |
| Glycerin/*Padina Pavonica* extract | 0.10 | 0.10 |
| Butylene glycol/Sea Whip (*Gorgonian*) extract (PLA-2 Pathway Inhibitor) | 0.50 | 0.50 |
| Water/decarboxy carnosine HCl/butylene glycol (Alistin) | 0.20 | 0.20 |
| *Camomilla Recutita* (*Matricaria*) Flower extract (COX-2 Pathway Inhibitor) | 0.017 | 0.012 |
| Water/butlene glycol/lecithin/C1-8 alkyl tetrahydroxycyclohexanoate/*Rosmarinus Officianalis* (Rosemary) extract/Ascorbyl tocopheryl maleate/maltodextrin/lauryldimonium hydroxypropyl hydrolyzed soy (Histamine Pathway Inhibitor) | 1.00 | |
| Water/butylene glycol/disodium NADH/lecithin/C1-8 alkyl tetrahydroxycyclohexanoate/*Rosmarinus Officinalis* (Rosemary) Extract, Ascorbyl tocopheryl maleate/maltodextrin/lauryldimonium hydroxypropyl hydrolyzed soy protein | | 1.00 |
| Dimethicone | 1.50 | |
| Dimethicone/Polysilicone-11 | | 6.00 |
| Silica | | 2.00 |
| Ammonium Acryloydimethyltaurate/VP Copolymer | 0.95 | 1.00 |
| Trehalose | 0.50 | 0.50 |
| PEG-100 stearate | 1.50 | |
| *Echinacea Pallida* (Coneflower) Extract (VEGF Pathway Inhibitor) | 0.001 | 0.001 |
| Zeolite | 0.10 | 0.10 |
| Phenoxyethanol | | 0.009 |
| Polysorbate 20 | | 0.20 |
| Disodium EDTA | 0.10 | |
| Algae Extract (Polysea PF) (Adhesion Pathway Inhibitor) | 0.50 | 0.50 |
| Polyester-8 | 3.00 | 2.32 |
| Linoleic acid | 0.20 | 0.20 |
| Glyceryl stearate | 1.50 | |
| Butylene glycol | 0.50 | 3.00 |
| Sucrose | 0.50 | 0.50 |
| Polyglyceryl-2 Triisostearate | 3.00 | |
| Avobenzone | 3.00 | 3.00 |
| Sodium Ribonucleic Acid | 0.20 | 0.20 |
| Tocopheryl acetate | 0.50 | 0.50 |
| Octocrylene | | 1.39 |
| Caprylyl glycol/phenoxyethanol/hexylene glycol | 0.80 | |
| Tromethane | 0.07 | 0.08 |
| Acrylamide/Sodium acryloyldimethyltaurate copolymer/Isohexadecane/Polysorbate 80 | 0.90 | |
| Acrylic acid/VP crosspolymer | | 0.10 |
| Behenyl alcohol | 1.00 | |
| Dimethicone | 3.00 | |
| Caffeine | 0.18 | 0.20 |
| Water/butylene glycol/*Laminaria Saccharina* extract | | 0.50 |
| Sodium hyaluronate | 0.10 | 0.01 |
| Benzophenone-3 | 5.00 | 5.00 |
| Water/lecithin/*micrococcus* lysate | 0.10 | 0.10 |
| Laureth-4 | | 0.685 |
| Dimethicone | 0.75 | |
| Butyloctyl salicylate | 3.50 | 3.50 |
| Isononyl isononanoate | | 3.00 |
| *Astrocaryum Murmuru* Butter | 0.20 | |
| Steareth-21 | 0.90 | |
| Polyethylene | 0.50 | 0.0001 |
| Isopropyl PPG-2-Isodeceth-7 Carboxylate | 3.50 | |
| Sodium chloride | 0.0001 | 0.0001 |

-continued

| Ingredient | w/w % | |
|---|---|---|
| | 1 | 2 |
| Petrolatum | 5.00 | |
| Sodium EDTA | | 0.10 |
| Glycerin | | 1.50 |
| Water | QS 100 | QS 100 |

Composition 1 contains 6 Pathway Inhibitors and Composition 2 contains 5 Pathway Inhibitors. The compositions are prepared by combining the ingredients and mixing well to form emulsions.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

The invention claimed is:

1. A method for treating intact irritated or inflamed skin by topically applying a composition that comprises:
   at least one Histamine pathway inhibitor in the form of a botanical extract having a component selected from the group consisting of flavones, apigenins, flavonoids, luteolins, phloretins, chalcones and mixtures thereof,
   at least one Phospholipase A2 pathway inhibitor in the form of a botanical extract having a component selected from the group consisting of amentoflavone, licochalcone, ellagic acid, hesperitin, polyphenol, and mixtures thereof,
   at least one Cyclooxygenase-2 pathway inhibitor in the form of a botanical extract selected from the group consisting of *Acacia* genus, *Calluna* genus, *Rosa* genus, *Polyporus* genus, *Chamomilla* genus, nettle leaf, Butcher's broom; hesperidin, methyl chalcone, resveratrol, HOPS beta acids, and mixtures thereof; and
   at least one Vascular Endothelial Growth Factor pathway inhibitor in the form of a botanical extract selected from the group consisting of *Saussurea* genus, *Magnolia* genus, *Cynara* genus, *Echineacea* genus, *Pallida* genus; sesquiterpene lactones, hypoestoxide, and mixtures thereof;
wherein the composition has an efficacy equal to or greater than a topically applied composition containing 1% hydrocortisone in ameliorating the adverse effects of skin irritation or inflammation when the composition is tested for such efficacy by applying same to a 1.5 inch square of the volar forearm and after 20 minutes 4 mg/cm$^2$ Balsam of Peru is applied in a 1.5 cm diameter circle to the site where the composition was applied and the degree of redness is measured with a chromameter.

2. The method of claim 1 wherein the composition additionally comprises one or more of the following:
   a Lipooxygenase pathway inhibitor,
   a Chemotaxis pathway inhibitor,
   an Adhesion pathway inhibitor,
   a Collagenase pathway inhibitor,
   an Elastase pathway inhibitor,
   a Phosphodiesterase pathway inhibitor; and
   a Histamine Receptor pathway inhibitor.

3. The method of claim 2 wherein one or more of the ingredients selected inhibit more than one of the pathways.

4. The method of claim 2 wherein the composition comprises all of the pathway inhibitors.

5. The method of claim 3 wherein the pathways inhibitors are present in an amount of 0.0001-75% by weight of the total composition.

6. The method of claim 1 wherein the Histamine pathway inhibitor is a flavone.

7. The method of claim 6 wherein the flavone is an amentoflavone or an extract from celery, parsley, or citrus fruits.

8. The method of claim 7 wherein the citrus fruit extract is from grapefruit.

9. A method for treating intact irritated or inflamed skin for redness, pain or heat by topically applying to the skin a composition comprising:
   at least one Histamine pathway inhibitor;
   at least one Phospholipase A2 pathway inhibitor,
   at least one Lipooxygenase pathway inhibitor,
   at least one Cyclooxygenase 2 pathway inhibitor,
   at least one Chemotaxis pathway inhibitor,
   at least one Adhesion pathway inhibitor,
   at least one Collagenase pathway inhibitor,
   at least one Elastase pathway inhibitor,
   at least one Phosphodiesterase A2 pathway inhibitor,
   at least one VEGF pathway inhibitor; and
   at least one Histamine receptor pathway inhibitor.

10. The method of claim 9 wherein the ingredient that inhibits the Phospholipase A2 pathway is selected from the group consisting of *Lyngbya* extract; grapeseed extract; licochalcone; *Viapure poria* extract; *Polyporus umbellatus*; avocado extract; *Camellia sinensis*; *Chrysanthellum indicum*; *Tridentata marginata* extract; Pomegranate extract; Gorgonian extract; and mixtures thereof.

11. The method of claim 9 wherein the ingredient that inhibits the Lipooxygenase pathway is selected from the group consisting of *Haplophyllum hispanicum* Spach; *Scutellaria Rivularis* extract; alpha ketoboswellic acid; (1-(1-benzothiophen-2-ylethyl)-1-hydroxy-urea); *Centaurium* extract; nordihydroguaiaretic acid; ginger oil; resveratrol; *Polygonum Cuspidatum* extract; cedar himalaya extract; tetrahydrocurcuminoids; *Nigella Sativa* essential oil; copaiba balsam; Australian sandalwood; *Rhodiola Rosea*; frankincense; blue cypress oil; blue chamomile oil; vetiver mada; bulgarian rose oil; Helichrysum oil; rosmarinic acid; resveratrol triphosphate; noni leaf extract, and mixtures thereof.

12. The method of claim 9 wherein the Cyclooxygenase-2 pathway inhibitor is selected from the group consisting of *Acacia* genus; *Calluna Vulgaris*; *Rosa Canina* fruit extract; nettle leaf extract; *Polyporus Umbellatus*; *Chamomilla Recutita* (Matricaria) flower oil; a mixture of Butcher's Broom extract and heperidin methyl chalcone; resveratrol; HOP's beta acids; and mixtures thereof.

13. The method of claim 9 wherein the Chemotaxis pathway inhibitor is selected from the group consisting of polysaccharides isolated from seaweeds such as kombu, limu, moui, bladderwrack, wakame, mozuku, hijiki; fucoidan; sea cucumber; kelp; sea buckthorn; *Laminaria Japonica*; *Fucus Vesiculosis*; extracts from onions, potatoes, celery, carrots, turnips, parsley, parsnip, sweet potato, yucca, or beets; licorice extracts; genestein; extracts from the genus *Scutellaria*; extracts from the *Boswellia* genus such as *Boswellia Serrata, Boswellia Bhau-dajiana, Boswellia Frereana, Boswellia Papyrifera, Sudanese Boswellia Sacra*, and *Boswellia Carteri*; *Commiphora Incisa*; *Commiphora Myrrha*; *Commiphora Abyssinica*; *Commiphora Erthraea*; *Commiphora Molmol*; *Bursera Microphylla*; *Nidularium Procerum*; sequoia extract; hypoestoxide; *Curcuma Longa* (turmeric) extract; butyloctyl salicylate; abyssine; plai oil; geranium bourbon oil; caffeine; galactoarabinan; lion's mane mushroom extract; clerilys; *Macrycystis Pyrifera* extract; reishi mushroom extract; *Pleurotus Ostreatus* extract; *Hypsizygus Ulmarius* extract; *Cladosiphon Okamuranus* extract; *Acalypha Wilkesiana* extract; *Acanthopanax Gracilistylus* extract; *Allium Sativum* extract; *Ananus Comosus* extract; *Cissampelos Sympodialis* extract; *Coriolus Versicolor* extract; *Echinacea Purpurea* extract; *Grifola Frondosa* extract; *Harpagophytum Procumbens* extract; *Panax Ginseng* extract; *Polygala Tenuifolia* extract; *Poria Cocos* extract; *Silybum Marianum* extract; *Smilax Glabra* extract; *Tinospora Cordfolia* extract; *Uncaria Tomentosa* extract; and *Withania Somnifera* extract; slime mold extract; *Echinancea* extract; *Viscum Album* extract; coffee robusta seed extract; capsaicin; and mixtures thereof.

14. The method of claim 9 wherein the Adhesion pathway inhibitor is selected from the group consisting Algae extract; neem oil limonoids; *Asparagus Racemusus* extract; *Platycodon* extract; Chaga Mushroom extract; *Emblica Officinalis* extract; *Criste Marine* extract; *Lavande Papillon* extract; *Polygonum Cuspidatum*; ginger; and mixtures thereof.

15. The method of claim 9 wherein the Collagenase pathway inhibitor is selected from the group consisting of *Siegesbeckia orientalis* extract; an extract from the *Doliocarpus* genus such as *Doliocarpus Verruculosus*; an extract from the *Kaempferia* genus such as *Kaempferia Galanga* root extract; an extract from the *Camilla* genus such as *Camilla Sinensis*; an extract from the *Sauropus* genus such as *Sauropus Androgynus*; an extract from the *Tetracapidium* genus such as *Tetracapidium Conophorum*; glucosamine; N-acetyl glucosamine; chondroitan sulfate; *Pinus Pinaster* (pine bark) extract; lysine; *Vitis Vinefera* (grape) seed extract; retinoids such as retinyl palmitate, retinol, retinoic acid; extracts from the *Pluchea* genus such as *Pluchea Indica* (Compositae); extracts from the *Viola* genus such as *Viola Hondoensis*; cocoa bean; extracts from the *Triphala* genus such as *Triphala Chebula*; anthocyanins; epigallocatechingallate; epicatechingallate; luteolin; *Citri Reticulatae* peel extract; winter begonia extract; extracts from the *Tepescohuite* genus such as *Tepescohuite* spray dried extract; extracts from the *Mimosa* genus such as *Mimosa Pudica* extract; picolinic acid; *Silymarin* extract, *Eucommia* extract, amentoflavone; from the *Menyanthes* genus such as *Menyanthes Trifoliate* extract; and mixtures thereof.

16. The method of claim 9 wherein the Elastase pathway inhibitor is selected from the group consisting of *Boswellia Serratia* extract; winter begonia extract; oleanolic acid; ursolic acid; phytocohesin; *Pygeum Africanum* extract; *Padina Pavonica* extract; *Actina Boswellia* extract; ligustrum; dipalmitoyl hydroxyproline; Soft pygeum extract; chaga mushroom extract; 7-DHC (7-dehydrocholesterol); white birch extract; polyphenon E; jojoba protein isolate; red raspberry powder; heather extract; hesperitin; hibiscin; a mixture of soybean protein and oxido reductases; grapeseed extract; a mixture of butcher's broom extract and hesperidin methyl chalcone; hesperidin; caffeine; a protein hydrolysate obtained from extracted organic germinated wheat seeds; hesperitin; glycine soja protein; jojoba oil; and a mixture of butylene glycol, water and Olea Europaea fruit extract.

17. The method of claim 9 wherein the Phosphodiesterase pathway inhibitor is selected from the group consisting of nordihydroguaiaretic acid; emodin (an extract from Rheum Emodi or rhubarb); 18-B-glycerrhetinic acid; caffeine; wild yam powder; *Anemarrhena asphodeloides* extract; *Zhi Mu* extract; *Eucomia* extract; *Uncaria tomentosa*; and mixtures thereof.

18. The method of claim 9 wherein the VEGF pathway inhibitor is selected from the group consisting of extracts from the *Saussurea* genus such as *Saussurea* Cost, *Saussurea Lappa*; Sesquiterpene lactones; magnolia extract; a mixture of butylene glycol, water, and *Cynara Scolymus* (Artichoke) Leaf Extract); hypoestoxide (HE); *Magnolia Officianalis* Bark extract; *Echineacea Pallida* extract; and mixtures thereof.

19. The method of claim 9 wherein the Histamine receptor pathway inhibitor is selected from the group Mangosteen, Japanese Butterbur extract, *Garcinia Mangostana* Peel Extract, and mixtures thereof.

20. The method of claim 9 wherein the formulated composition comprises:
 (a) a Histamine pathway inhibitor that is grapefruit peel extract,
 (b) a Phospholipase A2 pathway inhibitor that is Gorgonin extract,
 (c) a Lipooxygenase pathway inhibitor that is nordihydroguaiaretic acid,
 (d) a Cyclooxygenase 2 pathway inhibitor that is resveratrol,
 (e) a Chemotaxis pathway inhibitor comprising *Cladosiphon okamuranus* extract,
 (f) an Adhesion pathway inhibitor comprising algae extract,
 (g) a Collagenase pathway inhibitor comprising *Siegesbeckia orientalis* extract,
 (h) an Elastase pathway inhibitor comprising White birch extract,
 (i) a Phosphodiesterase A2 pathway inhibitor comprising B-glycyrrhetinic acid,
 (j) a VEGF pathway inhibitor comprising *Magnolia* extract; and
 (k) a Histamine receptor pathway inhibitor comprising *Garcinia mangostana* extract.

* * * * *